(12) United States Patent
Grendele et al.

(10) Patent No.: US 9,630,944 B2
(45) Date of Patent: Apr. 25, 2017

(54) PROCESS FOR PREPARING IMATINIB AND SALTS THEREOF, FREE OF GENOTOXIC IMPURITY F

(71) Applicant: F.I.S.—FABBRICA ITALIANA SINTETICI S.P.A., Montecchio, Maggiore (VI) (IT)

(72) Inventors: Ennio Grendele, Valdagno (IT); Alberto Soldà, Valdagno (IT)

(73) Assignee: F.I.S.—FABBRICA ITALIANA SINTETICI S.P.A., Montecchio Maggiore (VI) (IT)

( * ) Notice: Subject to any disclaimer, the term of this patent is extended or adjusted under 35 U.S.C. 154(b) by 0 days.

(21) Appl. No.: 14/619,542

(22) Filed: Feb. 11, 2015

(65) Prior Publication Data

US 2015/0299164 A1    Oct. 22, 2015

(30) Foreign Application Priority Data

Apr. 4, 2014   (IT) ............................... VI2014A0094

(51) Int. Cl.
    *C07D 401/04*    (2006.01)
(52) U.S. Cl.
    CPC .................. *C07D 401/04* (2013.01)
(58) Field of Classification Search
    CPC .................................................... C07D 401/04
    See application file for complete search history.

(56) References Cited

U.S. PATENT DOCUMENTS

2006/0223816 A1    10/2006   Adin et al.
2011/0306763 A1*   12/2011   Kamath et al. ............... 544/295

FOREIGN PATENT DOCUMENTS

| CN | 103058991 | * | 4/2013 |
|---|---|---|---|
| EP | 564409 | | 10/1993 |
| EP | 998473 | | 5/2000 |
| EP | 2546247 | | 1/2013 |
| IT | 1406881 | | 7/2011 |
| WO | 2006024863 | | 3/2006 |
| WO | 2008059551 | | 5/2008 |
| WO | 2008136010 | | 11/2008 |
| WO | WO2008136010 | * | 11/2008 |
| WO | 2008150481 | | 12/2008 |
| WO | 2011114337 | | 9/2011 |
| WO | 2012015999 | | 2/2012 |
| WO | 2012131711 | | 10/2012 |

OTHER PUBLICATIONS

CN103058991, 2013, machine translation, 9 pages.*
Amala Kompella, et al., A Facile Total Synthesis for Large-Scale . . . , Organic Process Research & Development, vol. 16, No. 11, pp. 1794-1804, 2012.
Search Report issued in corresponding Italian Patent Application No. VI2014A0094, filed Apr. 4, 2014.

* cited by examiner

*Primary Examiner* — Sun Jae Yoo
(74) *Attorney, Agent, or Firm* — Lucas & Mercanti, LLP

(57) ABSTRACT

The invention relates to an improved process for the preparation of Imatinib and salts thereof, in particular Imatinib Mesylate, having a content of a particular genotoxic impurity, named impurity F, within the pharmacopeia limits.

18 Claims, No Drawings

PROCESS FOR PREPARING IMATINIB AND SALTS THEREOF, FREE OF GENOTOXIC IMPURITY F

CROSS-REFERENCE TO RELATED APPLICATION

This application claims the benefit of priority from Italian Patent Application Serial No. VI2014A000094 filed Apr. 4, 2014, the contents of which are incorporated herein by reference.

TECHNICAL FIELD

The object of the present invention is a process for preparing Imatinib and salts thereof, in particular Imatinib Mesylate, having a content of a particular genotoxic impurity, called impurity F, within the limits of the pharmacopoeia.

BACKGROUND OF THE INVENTION

Imatinib or 4-[(4-methyl-1-piperazinyl)methyl]-N-[4-methyl-3-[[4-(3-pyridinyl)-2-pyrimidinyl]amino]phenyl]-benzamide, and in particular Imatinib mesylate of formula (I-MSA), is an important active substance used in the treatment of chronic myeloid leukemia.

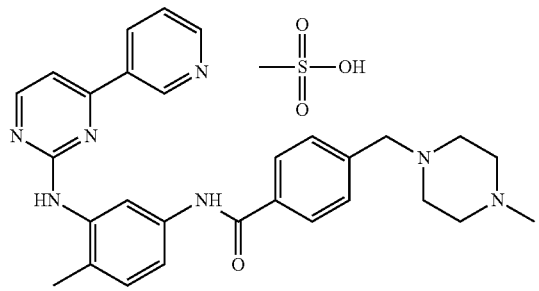

(I-MSA)

Its preparation is described for the first time in EP 564409.

An interesting and economical process for preparing a key intermediate of Imatinib: 4-methyl-N3-[4-(3-pyridinyl)-2-pyrimidinyl]-1,3-benzenediamine of formula (II):

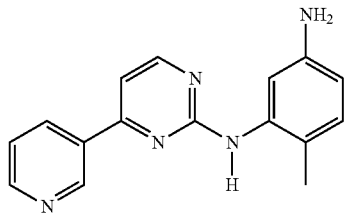

(II)

is described in WO2008/059551 of F.I.S.—Fabbrica Italiana Sintetici S.p.A.

EP998473 describes the preparations of the alpha and beta polymorphic form of Imatinib mesylate.

WO2006/024863, US2006/0223816, WO2008/150481 and WO2009/151899 also describe other preparations of polymorphic forms of Imatinib mesylate, of the alpha and beta forms in particular. This literature does not, however, highlight a major problem that cannot be ignored in a pharmaceutical context, which is that of residual solvents. Patents EP2546247 and IT1406881 B, also of F. I. S., describe a process for preparing the alpha and beta polymorphic form of Imatinib mesylate that allows a product, having residual solvents within the limits laid down by the ICH guideline, to be obtained.

The mutagenicity of the synthesis intermediate having formula (II), 4-methyl-N3-[4(3-pyridinyl)-2-pyrimidinyl]-1,3-benzenediamine, was extensively studied during the development of the synthesis process of Imatinib:

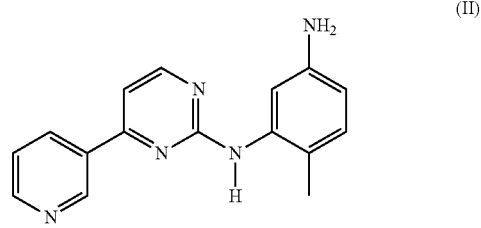 [SMILES: Cc1ccc(N)cc1Nc1nccc(-c2cccnc2)n1]

(II)

and it was found that it was positive for mutagenesis in that it provides a positive response to the Reverse Mutation Assay test using *Salmonella Typhimurium*.

The compound of formula (II) is the last intermediate in the synthesis of Imatinib and it is therefore of fundamental importance to ensure that the content of this residual reagent, a potential genotoxic impurity of Imatinib base and of Imatinib mesylate, is so low as to ensure the safety of the pharmaceutical product containing Imatinib mesylate.

It has been recently observed that at least one Regulatory Authority is considering a limit for this impurity, compound of formula (II) and impurity called impurity F of Imatinib, and this limit would be in the order of parts or of tens per million (ppm).

In the remaining part of the description, the compound of formula (II) can therefore also be called impurity F or aminopyrimidine.

The publication WO2012/015999, in example 1, discloses a process for the preparation of Imatinib by coupling of the compound of formula (II) with 4-((4-methylpiperazin-1-yl)methyl)benzoyl chloride where, during the work-up, Imatinib was transferred from and organic phase consisting of dichloromethane to an aqueous phase at pH 4.5-5.0, said pH being achieved by addition of 20% acetic acid solution. The aqueous phase has been washed three times with dichloromethane and at the end the product has been obtained with 66.8% of molar yield.

In example 9, a similar procedure of example 1 has been repeated, including the three washings of the aqueous phase with dichloromethane, providing Imatinib with molar yield of 64.0%. After recrystallization of the product using Dimethylformamide the product still contains 20 ppm of impurity F.

The main drawbacks of these procedures are the relatively low molar yield of the product, the need of preforming three washings of the aqueous phase, and the final product contains a relatively high amount of impurity F (20 ppm).

The publication WO2008/136010, example 1, discloses a process for the preparation of Imatinib by coupling of the compound of formula (II) with 4-((4-methylpiperazin-1-yl)methyl)benzoyl chloride where, during the work-up, Imatinib was transferred from and organic phase made of chloroform to an aqueous phase at pH 3-4, said pH being achieved by addition of dilute hydrochloric acid. The aqueous phase has been washed three times with chloroform.

WO2012/131711, example 1 and 2, disclose a process for the preparation of Imatinib by coupling of the compound of formula (II) with 4-((4-methylpiperazin-1-yl)methyl)benzoyl chloride where, during the work-up, Imatinib was transferred from and organic phase made of dichloromethane to an aqueous phase at pH 2.5-3.0, said pH being achieved by addition of dilute hydrochloric acid. The aqueous phase has been washed with dichloromethane thus providing Imatinib containing 13.3 or 29 ppm of impurity F. After recrystallization of the product using Methanol the Imatinib contains 2.6 or 9.0 ppm of impurity F it was obtained with a molar yield of 74% or 73%. Nevertheless, to achieve these levels of impurity F, a large excess (>1.5 mol. equivalents) of 4-((4-methylpiperazin-1-yl)methyl)benzoyl chloride have been used to reduce the amount of residual compound of formula (II) (i.e. impurity F) at the end of the coupling reaction.

The procedure disclosed in WO2012/131711 suffers therefore of some drawbacks, such as the need of use a large excess of 4-((4-methylpiperazin-1-yl)methyl)benzoyl chloride, the need of wash the aqueous phase with other dichloromethane, the molar yield is relatively low and the amount of impurity F, before the final crystallization is relatively high.

SUMMARY OF THE INVENTION

The problem addressed by the present invention is therefore that of making available an improved process for the preparation of Imatinib having a low amount of impurity F, with higher molar yields and avoiding the washings of the aqueous phase to reduce the amount of impurity F.

This problem is solved by a synthesis process of Imatinib and salts thereof as outlined in the accompanying claims, the definitions of which form an integral part of the present description.

Further characteristics and advantages of the process according to the invention will become apparent from the below-reported description of preferred embodiments, given by way of a non-limiting example.

DESCRIPTION OF THE INVENTION

The present invention includes a process for preparing Imatinib of formula (I) or salts thereof:

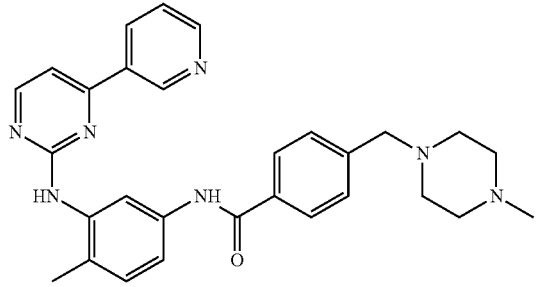
(I)

comprising the following steps:
a) reacting the compound of the formula (II):

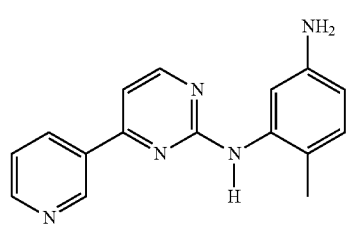
(II)

with the compound of formula (III) or salts thereof:

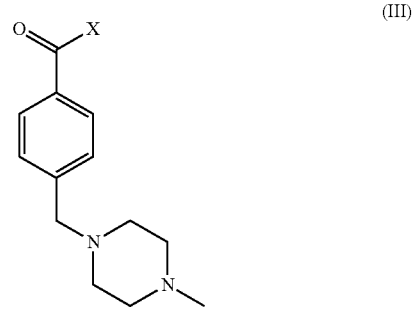
(III)

wherein X is selected from hydroxyl, chlorine, bromide or other leaving group, in an organic solvent to give Imatinib of formula (II); and
b) the transfer of the Imatinib of formula (I) from an organic phase to an aqueous phase having pH between 3.5 and 5.0.

Suitable organic solvents include, for example, THF, MeTHF or a mixture thereof, but the solvent for the reacting step a) is preferably but not required to be the same solvent for step b) organic phase.

In particular, the step b) includes the transfer of the Imatinib of formula (I) from an organic phase consisting of tetrahydrofuran (THF) or methyltetrahydrofuran (MeTHF) to an aqueous phase having a pH comprised between 3.5 and 5.0.

Surprisingly, it has in fact been found that by transferring the Imatinib from an organic phase to an aqueous phase having a pH between 3.5 and 5.0, it is possible to dramatically reduce the amount of the compound of formula (II):

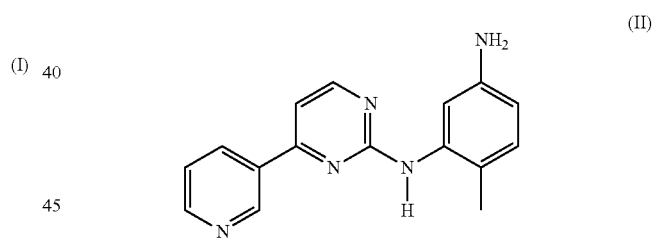
(II)

that is, of impurity F in the Imatinib to values under 40 ppm (ppm=parts per million), typically attaining quantities in the order of 6-12 ppm, without having to perform any further purification process.

The pH value of the aqueous phase in which Imatinib is transferred, that is to say, a pH between 3.5 and 5.0, is crucial and essential in order to allow the impurity F to be reduced to values under 40 ppm, and preferably to values under 20 ppm.

The basic concept of the present invention is as follows: the Imatinib base present in the organic phase together with the compound of formula (II), the latter at levels in the order of hundreds or thousands of ppm, is selectively and quantitatively transferred to the aqueous phase by means of the formation of an Imatinib salt while the impurity F remains, almost quantitatively, in the organic phase, thus obtaining an excellent separation of the two compounds.

This effective and efficient separation of the two similar compounds only and exclusively occurs if the pH of the aqueous phase is between 3.5 and 5.0.

On comparing the structures of Imatinib with that of the compound (II), namely, impurity F, it is noted that it cannot be immediately established that the two, chemically very similar, substances can be separated by an extraction in a well determined and controlled pH range.

By transferring Imatinib from an organic phase to an aqueous phase having a pH below 3.5, the impurity F is also transferred and in a much more consistent manner the lower the pH. See tests 3 and 4 of the table of example 3. In fact, as reported in this comparative table, by transferring Imatinib in aqueous phase at a pH between 0 and 3.5, Imatinib having values of impurity F in the order of hundreds or thousands of ppm of impurity F is obtained.

The transfer of Imatinib from an organic phase to an aqueous phase at a pH greater than 5 does not lead to satisfactory results because at this pH Imatinib is partially present as free base and therefore remains in the organic phase and being very insoluble in organic solvents, tends to precipitate as a solid. The Imatinib that remains in the organic phase and the Imatinib that precipitates as base causes reduced yield.

By performing the transfer (or extraction) of Imatinib from an organic phase in which it is present as an aqueous phase at a pH of between 3.5 and 5.0, the Imatinib almost quantitatively converts into a salt and the system is therefore sufficiently soluble and the impurity F, which is not salified, at the same time remains almost quantitatively in the organic phase thus allowing the impurity to be separated from the Imatinib.

The Imatinib present in the aqueous phase at a pH of between 3.5 and 5.0, and the impurity F that is present in the organic phase can therefore be separated by means of the further step of separation of the phases or by means of other techniques, such as continuous extraction, the addition of a different organic solvent that is partially soluble in water, which causes precipitation of the Imatinib salt or by means of the addition of an inorganic salt that saturates the aqueous phase thus increasing the ionic strength, without changing the pH, so as to cause precipitation of the Imatinib salt.

According to a preferred embodiment, the further step of separation of the phases is preferred in that it is very easy and economical.

Step (a) of the process of the present invention is carried out with a compound of formula (III) or salts thereof:

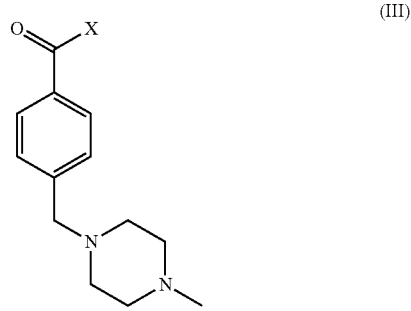

(III)

wherein X is selected from hydroxyl, chlorine, bromide or other leaving group.

Leaving group means any group used to activate the carboxyl function and therefore a group selected from the group comprising azides, substituted hydroxylamines (formed, for example with N-hydroxysuccinimide, 1-hydroxy-benzotriazole), fluoralcoholate esters (formed, for example, with trifluoroethanol), anhydrides (formed, for example, with pivaloyl chloride, ethyl chloroformate, etc.), esters with phenols (also replaced by electron-attractor groups, for example 2-hydroxypyridine), labile amides (formed, for example, with imidazole, triazines, etc.)

According to a preferred embodiment, the compound of formula (III) is one in which X is chlorine.

According to an even more preferred embodiment, the compound of formula (III) is one in which X is chlorine and being a dihydrochloride salt having stoichiometry (1:2), in other words, it is in dihydrochloride salt form.

Step a) wherein X is chlorine can be conveniently carried out in a solvent system consisting of THF or methyltetrahydrofuran, water and potassium carbonate.

Step a) is carried out in an organic solvent, preferably in THF or Methyltetrahydrofuran or mixtures thereof.

Step a) can also be carried out with the compound of formula (III) wherein X is OH, using a condensing agent such as, for example, a carbodiimide, like dicyclohexylcarbodiimide, or by means of propylphosphonic anhydride (T3P), 2-2-chloro methylpyridinium iodide, cyanuric chloride, 2-chloro-4,6-dimethoxy-1,3,5-triazine and phosphonium, uronium and guanidinium salts.

According to a preferred embodiment, step b) for the transfer of Imatinib of formula (I), is carried out from an organic phase to an aqueous phase having pH between 3.5 and 4.5. In fact, operating in this range, the Imatinib being almost entirely salified and in an aqueous phase, there is no need to heat the biphasic mixture to keep the Imatinib base in solution, which is necessary at a pH greater than 4.5, for example, operating at a pH between 4.5 and 5.0, since it is necessary to heat the mixture if the Imatinib base is to be kept unsalified in an organic solution. As can be seen in the table of example 3, operating between pH 4.5 and 5.0 the effect of removing the impurity F is always achieved, but the Imatinib product yield is lower as part of the Imatinib is lost in that it remains as a free base in the organic phase.

The pH range between 3.7 and 5.0 ensures that Imatinib is obtained with quantities of impurity F below 20 ppm without the need to perform any further recrystallization (see the table of example 3).

The pH range between 3.7 and 4.5 ensures that Imatinib is obtained with quantities of impurity F under 20 ppm without the need to operate any further recrystallization, and, at the same time, allows Imatinib to be maintained in solution without any need to heat and allows good yields to be achieved in terms of the Imatinib produced in that a relatively low amount of Imatinib remains as free base in the organic phase.

According to one preferred embodiment, the process of the present invention is carried out, in step b), at a pH between 3.8 and 4.2. This pH range provides the best results in terms of the low residual impurity F content and allowing the highest yields to be obtained in terms of the Imatinib produced.

According to a more preferred embodiment, the process of the present invention is carried out, in step b), at a pH of about 4.0.

According to a preferred embodiment, when step b) is carried out at a pH between 3.5 and 4.5, or more preferably at a pH between 3.8 and 4.2 or at about 4.0, the transfer of the Imatinib of formula (I) is carried out at a temperature between 10° C. and 30° C., preferably at about 20° C.

The process of the present invention is extremely efficient at removing the impurity F from Imatinib. In fact, it allows Imatinib mesylate to be purified in solution having even 1,000 ppm or up to 10,000 ppm of impurity F, obtaining solid Imatinib containing 6 to 12 ppm of impurity F. Such a surprising effect gives the great advantage of being able to carry out step a) for the synthesis of Imatinib using the compound of formula (III) in an amount from 1.2 to 1.4 molar equivalents with respect to the compound of formula (II), more preferably using approximately 1.3 molar equivalents. There is indeed no need to preventively reduce, that is to the level of step a) for the synthesis of Imatinib, the quantity of impurity F (starting compound of formula (II)), by means of the addition of a large excess of the other reactive, the compound of formula (III). The effect of purification in terms of impurity F supplied by the process of the present invention therefore allows the use, in step a) of the compound of formula (III) in an amount of 1.2 to 1.4 molar equivalents with respect to the compound of formula (II), since, although amounts of compound (II) in the order of thousands of ppm remain at the end of the reaction, they are effectively removed by step b). The fact of being able to operate with just 1.2-1.4 molar equivalents of compound (III), preferably with approximately 1.3 molar equivalents of compound (III), with respect to the compound (II), has obvious advantages in terms of the economic advantage of the entire preparation process of Imatinib.

The organic phase of step b) of the process of the present invention can be the same or can differ from that in which step a) was carried out.

The organic phase of step b) consists of one or more organic solvents. These solvents can be, for example, tetrahydrofuran, methyltetrahydrofuran or mixtures containing one of the same.

According to a preferred embodiment, the organic phase solvent consists of tetrahydrofuran.

In order for the aqueous phase to have a pH between 3.5 and 5.0, it can be prepared by adding an acid, such as, for example, hydrochloric acid, hydrobromic acid, sulphuric acid, etc. to the aqueous phase, preventively used, in conjunction with an organic phase, to perform step a). When the Imatinib is transferred in aqueous phase, it forms the corresponding salt, thus, depending on the acid used, Imatinib will be in the form of hydrochloride, hydrobromide, sulphate salt, etc.

According to a preferred embodiment, the aqueous phase at pH 3.5-5.0 of step b) is obtained by adding hydrochloric acid to the aqueous phase, thereby obtaining Imatinib hydrochloride in aqueous phase.

According to a preferred embodiment of the process of the invention, said process comprises the further step c) of separation of the phases and isolation of Imatinib or salts thereof.

Said further step c) can be carried out as here below explained: after having transferred, in other words extracted, Imatinib from the organic phase to the aqueous phase, the organic phase is separated, then the aqueous phase is brought to pH 8.5-9.0, which causes precipitation of the Imatinib base, which is then collected by filtration, washing with water and then with acetone, and then drying. Alternatively, following separation of the phases, the Imatinib can be brought to a new organic phase by basification of the aqueous phase, and can then be isolated from the organic phase with known organic synthesis techniques, for example by addition of methansulphonic acid, thus isolating Imatinib mesylate.

Where the transfer of Imatinib is carried out at a pH between 3.5 and 3.7, in order to reduce the quantity of impurity F to below 20 ppm it is sufficient to recrystallize the Imatinib base from methanol as described in the experimental part with a yield of around 90%.

The process of the present invention thus allows preparation of Imatinib base or salts thereof having an impurity F content in the Imatinib at values less than 20 ppm (ppm=parts per million), typically reaching quantities in the order of 6-12 ppm and, operating at pH between 3.7 and 5.0, without the need to further recrystallize the product.

A further advantage of the process of the present invention relates to the color of Imatinib. In fact, when Imatinib is transferred in an aqueous phase at pH 3.5-5.0, the solution remains almost colorless or, if anything, slightly yellowish, while if Imatinib is transferred in an aqueous phase having a pH lower than 3.5, the solution turns deep yellow to red in color, typically orange. Therefore, if Imatinib is precipitated by such an aqueous solution, for example by adding a cosolvent, operating in the pH range of the present invention, a significantly more colorless Imatinib is obtained.

The process yield of the present invention is between 86% and 94% when operating between pH 3.5 and 4.0. This yield significantly decreases when operating between pH 4.5 and 5.0 but is still useful.

According to a preferred embodiment, the process of the present invention can comprise a further recrystallization step of the Imatinib from methanol. The recrystallization of Imatinib base from methanol allows the impurity F content in the Imatinib to be halved. As recrystallizing Imatinib base has 6-12 ppm of impurity F with methanol, this therefore results in the latter dropping to values of 3-6 ppm in the Imatinib base. Recrystallization from methanol has a yield of 89-90%.

Lastly, crude Imatinib base or Imatinib base recrystallized from methanol by the methods described above can be converted into a salt thereof, preferably into mesylate salt, by means of the processes of the prior art. In particular, the procedures of the examples of EP2546247A1, the contents of which are incorporated herein by reference, can also be used. The Imatinib mesylate thus produced has an impurity F content equal to 4 ppm or 5 ppm. In addition, the Imatinib mesylate thus obtained has an alpha or beta crystalline form depending on the seeding used for its preparation, and has residual solvents within ICH limits, which is a significant issue for Imatinib mesylate and, lastly, is free of impurities such as esters of methanesulfonic acid.

The process of the present invention is particularly efficient to remove selectively the impurity F, limiting the loss of the product Imatinib. In other words, the impurity F tends to be completely extracted in the organic phase while Imatinib, as salts, tends to be completely retained by the aqueous phase.

This effect of removing very efficiently the impurity F is due to the combination of the particular range of pH selected, i.e. 3.5 to 5.0 and to the particular solvent selected, i.e. tetrahydrofuran or methyltetrahydrofuran.

As consequence of such efficiency and, consequently, as advantage of the process of the present invention, is not necessary to perform any washing of the aqueous phase after the separation of the organic phase, moreover, since Imatinib is not lost in the organic phase, the molar yield of the process is particularly high. Finally, the preparation of Imatinib with a low level of impurity F is achieved by the efficient process of the invention, based on a particular range of pH combined with specific extracting solvents such as tetrahydrofuran or methyltetrahydrofuran, and is not based on the use of a large excess of the chlorinating reagent as done in WO2012/131711, the contents of which are incorporated herein by reference, to reduce the residual amount of impurity F at the end of the coupling reaction.

According to an embodiment of the process of the present invention, in the step a) the pH from 3.5 to 5.0 of the aqueous phase is realized by addition of aqueous HCl 32% to the aqueous solution containing potassium carbonate. In such a way, Imatinib is transferred in the aqueous phase forming there a salt of Imatinib, in particular, forming Imatinib hydrochloride.

According to a preferred embodiment of the process of the invention, the volume of the organic phase is comprised from 4.5 to 6.5 volumes compared to the stoichiometric amount of Imatinib.

The stoichiometric amount of Imatinib means the theoretical amount of Imatinib that could be present in the reaction mixture if the all the amount of the minority reagent (in terms of moles) could be converted in Imatinib.

Volumes means the volumes of solvent per weight of product, for example 1 volume is 1 liter per 1 kilogram of product (Imatinib in this case) or is 10 ml per 10 grams or is 500 microliter per 500 mg. For example, 10 volumes are 100 liters per 10 kilograms of product.

In the above embodiment, 4.5 to 6.5 volumes compared to the stoichiometric amount of Imatinib, means that, for example, are used from 4.5 liters to 6.5 liters of organic phase per 1 Kilogram of stoichiometric Imatinib.

According to a more preferred embodiment of the process of the invention, the volume of the organic phase is about 5.6 volumes compared to the stoichiometric amount of Imatinib.

According to a preferred embodiment of the process of the invention, the volume of the aqueous phase is comprised from 4.5 to 6.5 volumes compared to the stoichiometric amount of Imatinib.

According to a more preferred embodiment of the process of the invention, the volume of the aqueous phase is about 5.6 volumes compared to the stoichiometric amount of Imatinib.

According to a preferred embodiment of the process of the invention, the volume of the organic phase is comprised from 4.5 to 6.5 volumes and the volume of the aqueous phase is comprised from 4.5 to 6.5 volumes both compared to the stoichiometric amount of Imatinib.

According to a more preferred embodiment of the process of the invention, the volume of the organic phase is about 5.6 volumes and the volume of the aqueous phase is about 5.6 volumes both compared to the stoichiometric amount of Imatinib.

According to a preferred embodiment of the process of the present invention, in the step b) the pH is comprised between 3.5 and 4.5 and the volume of the organic phase is comprised from 4.5 to 6.5 volumes compared to the stoichiometric amount of Imatinib.

The optimal embodiments, variables, and conditions of the process of the present invention, as described above and in the examples, can be combined in all possible combinations, which are therefore intended as being included in the description of the present invention.

EXPERIMENTAL SECTION

The starting material, 4-[(4-methyl-1-piperazinyl) methyl]-benzoic acid, hydrochloride (1:2), is a substance that is widely commercially available.

Example 1

Synthesis of 4-[(4-methyl-1-piperazinyl)methyl]-benzoyl chloride hydrochloride (1:2) of formula (III) with X=Cl

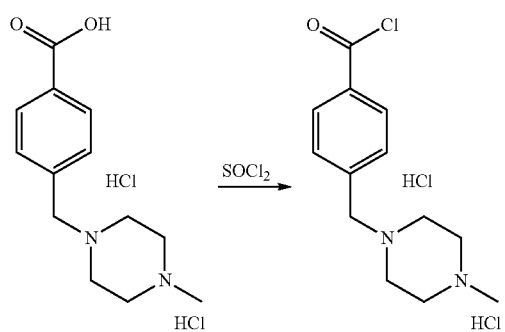

50 g of 4-[(4-methyl-1-piperazinyl)methyl]-benzoic acid, hydrochloride (1:2), were loaded into a reactor under nitrogen at 20° C. 200 g of thionyl chloride (SOCl$_2$) and 12.5 ml of dimethylformamide (DMF) were added, while maintaining a temperature below 25° C. The reaction mixture was stirred and heated to 65° C. for about 13 hours then cooled to 20° C. and the excess thionyl chloride was removed by distillation. The residue was dissolved in 100 ml of methylene chloride and the reaction mixture was stirred for 1 hour. The crystallized product was filtered, washed with 15 ml of methylene chloride and vacuum dried at 40° C. for 1 hour; 52 g of 4-[(4-methyl-1-piperazinyl)methyl]benzoyl chloride, hydrochloride (1:2) were obtained as a white powder.

Example 2

Synthesis of Crude Imatinib (Base)

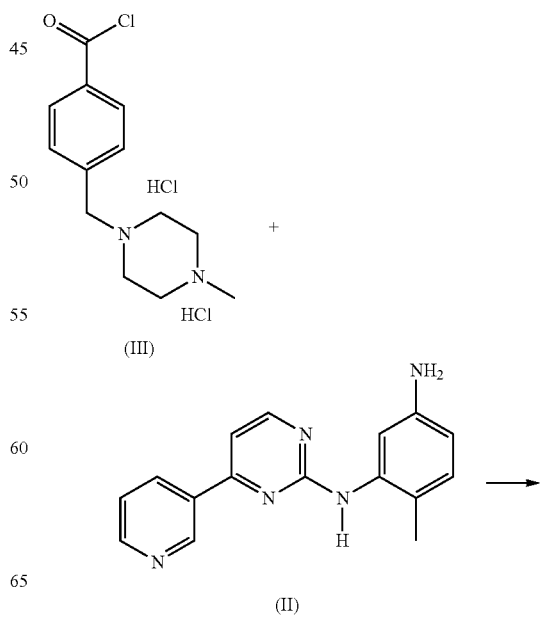

-continued

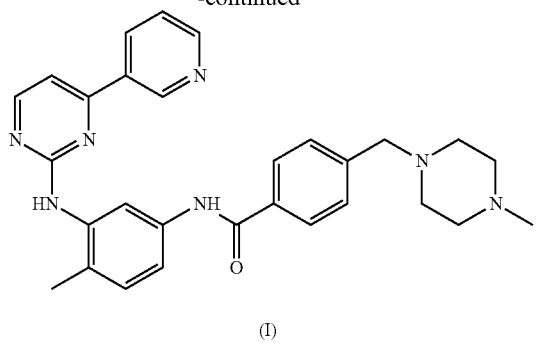

(I)

55.1 g of 4-[(4-methyl-1-piperazinyl)methyl]-benzoyl chloride, hydrochloride (1:2) of formula (III), in other words, 169.2 mmol (1.3 molar equivalents with respect to the compound of formula (II); 36 g of 4-methyl-N3-[4-(3-pyridinyl)-2-pyrimidinyl]-1,3-benzenediamine of formula (II) (prepared according to the teachings of WO2008/059551), in other words 129.8 mmol; 83 g of potassium carbonate and 360 ml of tetrahydrofuran (THF), were loaded into a reactor under nitrogen at 20° C.

The reaction mixture was stirred and heated to reflux (about 65° C.) for about 14 hours. The reaction is deemed complete when the compound of formula (II) is less than 1% (HPLC A %), in other words, less than 10,000 ppm of impurity F. The reaction mixture was then cooled to 20° C. and 20 ml of water were slowly added, over about 15 minutes 280 ml of water were subsequently added at 20° C. over 10 minutes. The reaction mixture was then brought to pH=4.0 with 90 ml of HCl 32%, obtaining two clear phases. The reaction mixture was stirred for about 20 minutes and then the phases were separated. The aqueous phase was basified to pH=8.5-9.0 with 40 ml of aqueous NaOH 30%, obtaining the crystallization of the product. The reaction mixture was stirred and heated at room temperature for about 45 minutes. The product was then filtered and washed twice with a mixture consisting of 50 ml of demineralized water and 1 ml of aqueous NaOH 30%. The product was then washed with 50 ml of acetone and vacuum dried at 50° C. for 12 hours; 57 g of crude Imatinib base were obtained.

Example 3

Synthesis of Crude Imatinib (Base)

Example 2 above was repeated while keeping all the other conditions unchanged and changing only the molar equivalents of compound (III) and/or the pH of the aqueous phase. The following table summarizes the results achieved.

| Test | Mol. Eq. of compound (III) over compound (II) | aqueous phase pH | Impurity F (Compound (II)) ppm | Yield (Isolated Imatinib base) |
|---|---|---|---|---|
| 1 | 2.3 | 2.5 | 8.18 | 68.5% |
| 2 | 3 | 2.5 | 6.33 | 69.1% |
| 3 | 1.2 | 2.5 | 212.66 | 78.2% |
| 4 | 1.3 | 3.0 | 63.8 | 82.2% |
| 5 | 1.3 | 3.5 | 36.96 | 86.4% |
| 6 | 1.3 | 4.0 | 10.56 | 91.8% |
| 7 | 1.3 | 4.0 | 8.85 | 93.6% |
| 8 | 1.2 | 4.0 | 7.00 | 90.4% |
| 9 | 1.3 | 4.5 | 6.03 | 78.5% |
| 10 | 1.3 | 5.0 | 5.84 | 54.4% |

Example 4

Synthesis of Purified Imatinib (Base)

57 g of crude Imatinib base and 1140 ml of methanol were loaded into a reactor under nitrogen at 20° C. The reaction mixture was stirred and heated to reflux (about 65° C.) obtaining dissolution of the crude Imatinib. The reaction mixture was stirred at this temperature for 15 minutes, then briefly cooled and then the solvent was distilled off, leaving a residue of 4 volumes. The reaction mixture was stirred and cooled to room temperature in 30', then stirred for at least 1 hour, to complete crystallization. The product was filtered, washed with 30 ml of Methanol and vacuum dried for 12 hours; 48 g of purified crude Imatinib base were obtained as a beige-colored solid crystalline.

Example 5

Determination of the Impurity F in the Imatinib, by Means of HPLC-MS

Column: X-Earth MS C18, 150 mm/3 mm/3.5 μm

Column temperature: 40° C.

Mobile phase A: Ammonium formate 1.26 g/L in water (pH 3.5 with formic acid).

Mobile phase B: ACN+0.05% formic acid

Gradient:

| Time (min) | % A | % B |
|---|---|---|
| 0 | 80 | 20 |
| 6 | 80 | 20 |
| 10 | 20 | 80 |
| 15 | 20 | 80 |

Flow: 0.5 ml/min

Detector: MS SIM 278.2 ESI-Positive

Injection volume: 10 μL

Example 6

Synthesis of Crude Imatinib (Base)

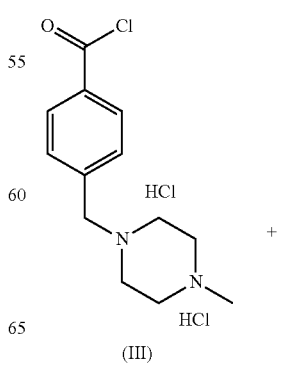

(III)

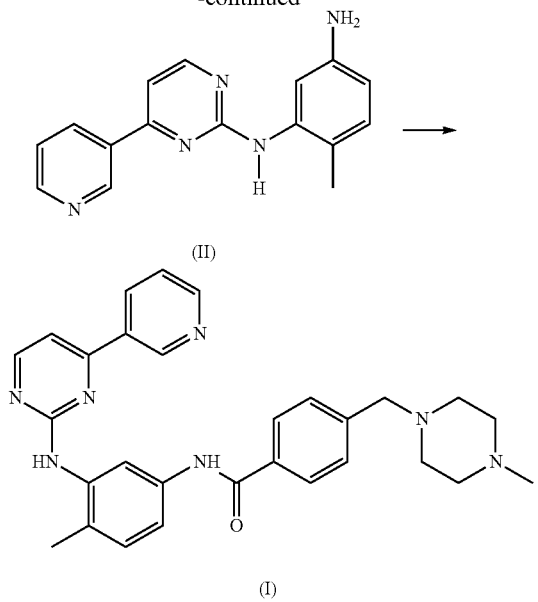

(II)

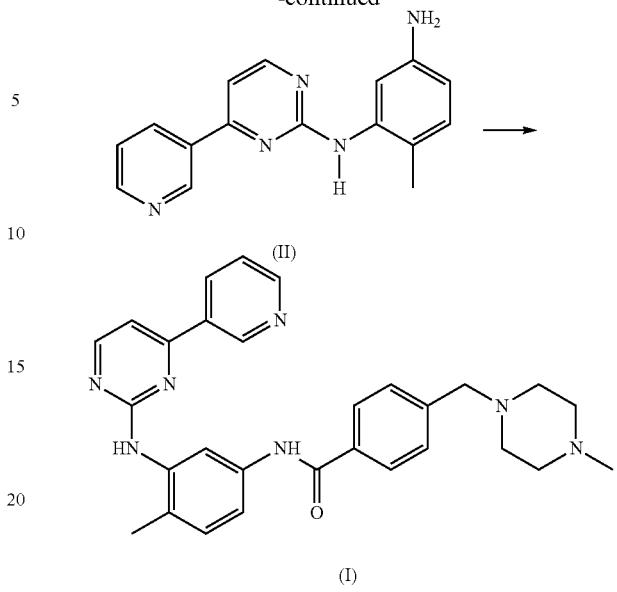

(II)

(I)

(I)

49.9 g of 4-[(4-methyl-1-piperazinyl)methyl]-benzoyl chloride, hydrochloride (1:2) of formula (III), in other words, 153.2 mmol (1.328 molar equivalents with respect to the compound of formula (II); 32 g of 4-methyl-N3-[4-(3-pyridinyl)-2-pyrimidinyl]-1,3-benzenediamine of formula (II) (prepared according to the teachings of WO2008/059551), in other words 115.4 mmol; 74 g of potassium carbonate and 320 ml of tetrahydrofuran (THF), were loaded into a reactor under nitrogen at 20° C.

The reaction mixture was stirred and heated to reflux (about 65° C.) for 17 hours. (HPLC area %=0.76% of impurity (F). The reaction mixture was then cooled to 20° C. and 247 ml of water were slowly dripped, in about 45 minutes. The reaction mixture was then brought to pH=4.0, in about 35 minutes, with 57 ml of HCl 32%, obtaining two clear phases. The reaction mixture was stirred for about 20 minutes and then the phases were separated. The aqueous phase was basified to pH=8.5-9.0 with 40 ml of aqueous NaOH 30%, obtaining the crystallization of the product. The reaction mixture was stirred and heated at room temperature for about 45 minutes. The product was then filtered and washed with a mixture consisting of 50 ml of demineralized water and 0.5 ml of aqueous NaOH 30%. The product was then washed with 30 ml of acetone and vacuum dried at 50° C. for 12 hours; 51.2 g of crude Imatinib base were obtained (molar yield: 85.4%; titre HPLC area %: 99.8%; loss on drying: 2.13%; residue on ignition: 0.15%; impurity F: 8.56 Ppm).

Example 7

Synthesis of Crude Imatinib (Base)

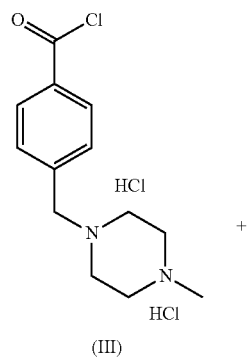

(III)

936.4 g of 4-[(4-methyl-1-piperazinyl)methyl]-benzoyl chloride, hydrochloride (1:2) of formula (III), in other words, 2.875 moles (1.329 molar equivalents with respect to the compound of formula (II); 600 g of 4-methyl-N3-[4-(3-pyridinyl)-2-pyrimidinyl]-1,3-benzenediamine of formula (II) (prepared according to the teachings of WO2008/059551), in other words 2.164 moles; 1380 g of potassium carbonate and 6000 ml of tetrahydrofuran (THF), were loaded into a reactor under nitrogen at 20° C.

The reaction mixture was stirred and heated to reflux (about 65° C.) for about 14 hours. (HPLC area %=0.76% of impurity (F). The reaction mixture was then cooled to 20° C. and 1000 ml of water were slowly added, in about 45 minutes. 3500 ml of water were subsequently added at 20° C. over 120 minutes. The reaction mixture was then brought to pH=4.0, in about 35 minutes, with 1440 ml of HCl 32%, obtaining two clear phases. The reaction mixture was stirred for about 20 minutes and then the phases were separated. The aqueous phase was basified to pH=8.5-9.0 with about 600 ml of aqueous NaOH 30%, obtaining the crystallization of the product. The reaction mixture was stirred and heated at room temperature for about 45 minutes. The product was then filtered and washed with a mixture consisting of 1000 ml of demineralised water and 10 ml of aqueous NaOH 30%. The product was then washed with 500 ml of acetone and vacuum dried at 50° C. for 12 hours; 980 g of crude Imatinib base were obtained (molar yield: 91.8%; titre HPLC area %: 99.8%; loss on drying: 2.45%; residue on ignition: 0.13%; impurity F: 10.56 Ppm).

Example 8

Synthesis of Purified Imatinib (Base)

950 g of crude Imatinib base (with 10.56 ppm of impurity F) and 18525 ml of methanol were loaded into a reactor under nitrogen at 20° C. The reaction mixture was stirred and heated to reflux (about 65° C.) obtaining dissolution of the crude Imatinib. The reaction mixture was stirred at this temperature for 15 minutes, then briefly cooled and then the solvent was distilled off, leaving a residue of 4 volumes. The reaction mixture was stirred and cooled to room temperature in 30', then stirred for about 1 hour, to complete crystallization. The product was filtered, washed with 475 ml of Methanol and vacuum dried for 12 hours; 845 g of purified crude Imatinib base were obtained as a beige-colored solid crystalline. (molar yield: 88.9%; titre HPLC area %: 99.9%; loss on drying: 0.15%; impurity F: 5.71 ppm).

Example 9

Synthesis of Crude Imatinib Base in Me-THF

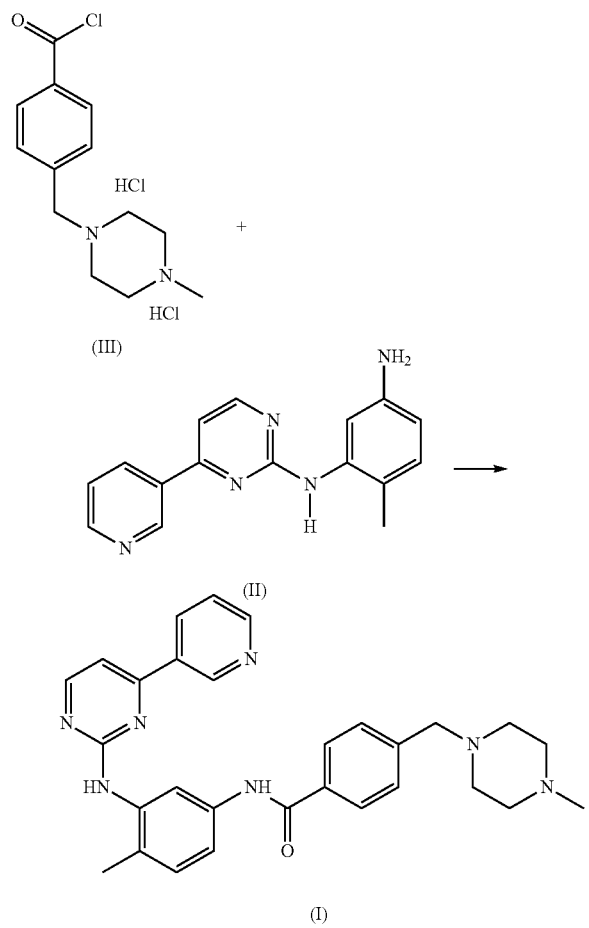

A 4-neck-RBF, under nitrogen atmosphere at 20° C., was charged with 14.1 g of 4-[(4-methyl-1-piperazinyl)methyl]-benzoyl chloride, hydrochloride (1:2) of formula (III), correspondent to 43.3 mmol, (1.3 molar equivalents compared to the compound of formula (II)); 10 g of 4-methyl-N3-[4-(3-piridinyl)-2-pirimidinyl]-1,3-benzendiamine of formula (II) (prepared according to the teachings of WO2008/059551), correspondent to 36.1 mmol; 19 g of potassium carbonate and 250 mL di methyltetrahydrofuran (Me-THF). The reaction mixture was stirred and heated till reflux temperature (about 80° C.) for about 14 hours. The reaction was deemed terminated when the compound of formula (II) was lower than 1% (HPLC A %), i.e. lower than 10.000 ppm of impurity F. The reaction mixture was then cooled down at 20° C. and, in about 15 minutes, 20 mL of water were slowly added. Later, at 20° C. in 10 minutes, 100 mL of water were slowly added. The reaction mixture was brought at pH=4.0 by addition of 22.5 mL of HCl 32%, obtaining clear phases. The reaction mixture was stirred for about 20 minutes and then the phases were separated. The aqueous phase was basified at pH=8.5-9.0 with 16 mL of aqueous NaOH 30%, obtaining the crystallization of the product. The reaction mixture was stirred at room temperature for about 45 minutes. Then the suspension was filtered and the solid was washed two times with a mixture composed by 20 mL of demineralized water and 0.5 mL of aqueous NaOH 30%. Later, the product was washed with 30 mL of acetone and dried at 50° C. for 12 hours under vacuum; 16.7 g of crude Imatinib base were obtained.

Example 10

Synthesis of Purified Imatinib (Base)

A reactor under nitrogen at 20° C. was charged with 16.7 g of crude Imatinib base prepared in example 9 and 335 mL of methanol. The reaction mixture was stirred and heated until reflux temperature (about 65° C.) obtaining the dissolution of the crude Imatinib. The mixture was stirred at said temperature for 15 minutes, then the solvent was distilled leaving 4 volumes of residual solvent. The reaction mixture was stirred and cooled down in 30 minutes till room temperature, then, stirred for at least 1 hour to complete the crystallization. The suspension was filtered and the solid was washed with 15 mL of Methanol and dried at 50° C. for 12 hours under vacuum; 14.8 g of purified Imatinib base were obtained as off-white crystalline solid. (Imp F 9.8 ppm).

Example 11

Synthesis of Purified Imatinib (Base) with Different Solvents

The examples 9 and 10 have been repeated consecutively only changing the solvent used to perform the coupling reaction and then the phase separations in the example 9.

| OPERATION | SOLVENT | YIELD | HPLC(A %) | IMP F |
|---|---|---|---|---|
| RD/070/1073/0408 | $CH_2Cl_2$ | 69.83% | 98.35 | 8.3 ppm |
| RD/070/1073/0435 | Toluene | 21.91% | 89.73 | 10.10% |
| RD/070/1098/0465 | Me—THF | 83.25% | 99.45 | 9.8 ppm |
| RD/070/1098/0509 | THF | 83.86% | 99.84 | 8.8 ppm |

The invention claimed is:
1. Process for the preparation of Imatinib of formula (I) or a salt thereof:

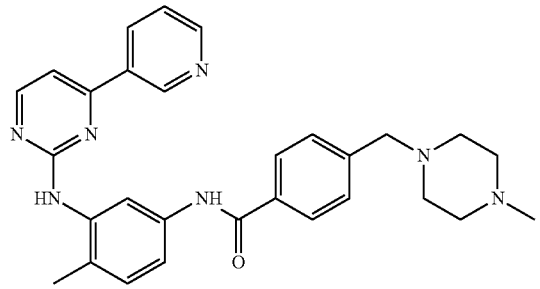

comprising:
a) reacting of a compound of formula (II):

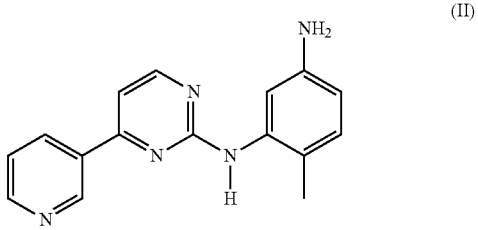 [SMILES: Cc1ccc(N)cc1Nc1nccc(-c2cccnc2)n1]

with a compound of formula (III) or a salt thereof:

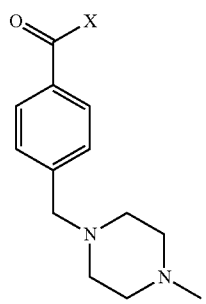

wherein X is hydroxyl, chlorine, bromine or other leaving group,
in an organic solvent,
to yield the Imatinib of formula (I),
b) transferring the Imatinib of formula (I) from an organic phase to an aqueous phase having a pH of between 3.5 and 5.0,
c) separating the organic phase and the aqueous phase, and
d) isolating the Imatinib or salt thereof,
wherein the organic phase contains tetrahydrofuran or methyltetrahydrofuran; and
wherein the level of impurity F in the Imatinib is less than 40 ppm.

2. Process of claim 1, wherein the organic solvent is tetrahydrofuran or methyltetrahydrofuran.

3. Process according to claim 1, wherein X is chlorine.

4. Process according to claim 1, wherein the pH is between 3.5 and 4.5.

5. Process according to claim 4, wherein the pH is between 3.8 and 4.2.

6. Process according to claim 1, wherein the transferring of the Imatinib of formula (I) is carried out at a temperature of between 10° C. and 30° C.

7. Process according to claim 1, wherein the compound of formula (III) is used in an amount of from 1.2 to 1.4 molar equivalents with respect to the compound of formula (II).

8. Process according to claim 7, wherein the compound of formula (III), is used in an amount of from 1.25 to 1.35 molar equivalents with respect to the compound of formula (II).

9. Process according to claim 1, wherein the volume of the organic phase is from 4.5 to 6.5 volumes compared to the stoichiometric amount of Imatinib.

10. Process according to claim 9, wherein the volume of the organic phase is about 5.6 volumes compared to the stoichiometric amount of Imatinib.

11. Process according to claim 1, wherein the volume of the aqueous phase is from 4.5 to 6.5 volumes compared to the stoichiometric amount of Imatinib.

12. Process according to claim 1 wherein the volume of the aqueous phase is about 5.6 volumes compared to the stoichiometric amount of Imatinib.

13. Process according to claim 1 wherein the volume of the organic phase is from 4.5 to 6.5 volumes and the volume of the aqueous phase is from 4.5 to 6.5 volumes, both compared to the stoichiometric amount of Imatinib.

14. Process according to claim 13 wherein in the volume of the organic phase is about 5.6 volumes and the volume of the aqueous phase is about 5.6 volumes both compared to the stoichiometric amount of Imatinib.

15. Process according to claim 1 wherein the pH is between 3.5 and 4.5 and the volume of the organic phase is from 4.5 to 6.5 volumes compared to the stoichiometric amount of Imatinib.

16. Process according to claim 1, wherein the level of impurity F in the Imatinib is less than 20 ppm.

17. Process according to claim 16, wherein the amount of impurity F in the Imatinib is 6-12 ppm.

18. Process according to claim 1, wherein the yield of Imatinib of formula (I) or a salt thereof is or exceeds 83.25%.

* * * * *